US008888842B2

(12) United States Patent
Gulcher

(10) Patent No.: US 8,888,842 B2
(45) Date of Patent: Nov. 18, 2014

(54) IMPLANT MADE OF A METALLIC MATERIAL WHICH CAN BE RESORBED BY THE BODY

(75) Inventor: Manfred Gulcher, Raesfeld-Erie (DE)

(73) Assignee: Qualimed Innovative Medizin-Produkte GmbH (DE)

( * ) Notice: Subject to any disclaimer, the term of this patent is extended or adjusted under 35 U.S.C. 154(b) by 288 days.

(21) Appl. No.: 13/379,230

(22) PCT Filed: Jun. 21, 2010

(86) PCT No.: PCT/EP2010/003723
§ 371 (c)(1),
(2), (4) Date: Feb. 23, 2012

(87) PCT Pub. No.: WO2010/145842
PCT Pub. Date: Dec. 23, 2010

(65) Prior Publication Data
US 2012/0143318 A1    Jun. 7, 2012

(30) Foreign Application Priority Data
Jun. 19, 2009 (DE) .......................... 10 2009 025 511

(51) Int. Cl.
| | |
|---|---|
| *A61F 2/06* | (2013.01) |
| *A61L 27/04* | (2006.01) |
| *A61L 31/02* | (2006.01) |
| *A61L 31/14* | (2006.01) |
| *A61L 27/58* | (2006.01) |

(52) U.S. Cl.
CPC ............. *A61L 27/047* (2013.01); *A61L 31/022* (2013.01); *A61L 31/148* (2013.01); *A61L 27/58* (2013.01)
USPC ........................................ 623/1.46; 623/1.15

(58) Field of Classification Search
CPC .............. A61F 2310/0041; A61F 2310/00425; A61F 2310/00197
USPC .......................................... 623/1.46; 420/405
See application file for complete search history.

(56) References Cited

U.S. PATENT DOCUMENTS

| | | | | |
|---|---|---|---|---|
| 3,687,135 | A * | 8/1972 | Stroganov et al. ............... | 606/76 |
| 4,401,621 | A * | 8/1983 | Unsworth et al. ............ | 420/403 |
| 5,073,207 | A * | 12/1991 | Faure et al. .................... | 148/667 |
| 5,077,138 | A * | 12/1991 | Hino et al. ..................... | 428/614 |
| 5,326,528 | A * | 7/1994 | Makino et al. ................. | 420/411 |
| 5,348,591 | A * | 9/1994 | Masumoto et al. ............ | 148/403 |
| 6,193,817 | B1 * | 2/2001 | King et al. ..................... | 148/420 |
| 7,682,470 | B2 * | 3/2010 | Bettles et al. .................. | 148/420 |
| 7,718,118 | B2 * | 5/2010 | Bronfin et al. ................. | 420/406 |
| 8,202,477 | B2 * | 6/2012 | Papirov et al. ................. | 420/402 |
| 8,268,235 | B2 * | 9/2012 | Gerold .......................... | 420/406 |
| 8,425,835 | B2 * | 4/2013 | Harder et al. .................. | 420/402 |
| 2002/0004060 | A1 * | 1/2002 | Heublein et al. .............. | 424/422 |
| 2008/0033530 | A1 * | 2/2008 | Zberg et al. ................... | 623/1.15 |
| 2008/0033531 | A1 * | 2/2008 | Barthel et al. ................. | 623/1.15 |
| 2008/0033539 | A1 * | 2/2008 | Sternberg et al. ............. | 623/1.46 |
| 2008/0071349 | A1 * | 3/2008 | Atanasoska et al. .......... | 623/1.15 |
| 2008/0082162 | A1 * | 4/2008 | Boismier et al. .............. | 623/1.38 |
| 2008/0208313 | A1 * | 8/2008 | Yu et al. ........................ | 623/1.15 |
| 2008/0243242 | A1 * | 10/2008 | Kappelt et al. ................ | 623/1.46 |
| 2008/0312736 | A1 * | 12/2008 | Mueller et al. ................ | 623/1.46 |
| 2009/0005862 | A1 * | 1/2009 | Nakatani et al. .............. | 623/1.49 |
| 2009/0171452 | A1 * | 7/2009 | Yamamoto et al. ........... | 623/1.38 |
| 2010/0249904 | A1 * | 9/2010 | Takayuki et al. .............. | 623/1.16 |
| 2011/0048169 | A1 * | 3/2011 | Stolfig .............................. | 75/302 |
| 2012/0195787 | A1 * | 8/2012 | Huang et al. .................. | 420/406 |
| 2013/0261735 | A1 * | 10/2013 | Pacetti et al. ................. | 623/1.36 |

FOREIGN PATENT DOCUMENTS

WO    WO 2009026652 A1 *    3/2009    ............. C22C 23/04

* cited by examiner

*Primary Examiner* — Thomas J Sweet
*Assistant Examiner* — Seema Mathew
(74) *Attorney, Agent, or Firm* — Berliner & Associates

(57) ABSTRACT

The invention relates to an implant consisting of a metallic magnesium alloy that can be resorbed by the body, said metallic material being a magnesium alloy consisting of at least 96% w/w of magnesium, at least 1% w/w of manganese and at least 0.5% w/w of at least one metal of the rare earth group.

9 Claims, No Drawings

IMPLANT MADE OF A METALLIC MATERIAL WHICH CAN BE RESORBED BY THE BODY

The invention relates to an implant made of metallic material that can be resorbed by the body, said material being present in the form of a magnesium alloy.

Implants capable of being resorbed in the body of a patient have basically been known for quite some time. Implants of this kind are for one thing made of bio-compatible and bioresorbable plastic materials, for example of polyactides and polyglycolides which, for instance, are used for the purpose of coating stents and are capable of dissolving over a shorter or longer period of time and during this process liberating the active agents they contain. It was also proposed to manufacture implants, for example stents, that consisted altogether of such plastic materials.

Resorbable implants consisting of metallic materials have been proposed on various occasions but have not found widespread acceptance hitherto. As an example, publication EP 0 923 389 describes a pure ion stent which is almost completely degradable in vivo over a time span ranging between four and twelve weeks. It must be borne in mind, however, that the degradation patterns arising during the biological degradation of such a stent structure very often show filigree peaks that subsequently may be the cause of vessel injuries.

According to EP 1 270 023 A2 medical implants can be manufactured from a range of magnesium alloys which may, inter alia, contain lithium, aluminum, rare earth metals, manganese, zinc or other metals. Explicitly described are alloys consisting of 8.5 to 9.5% of aluminum, 0.15 to 0.4% of manganese, 0.45 to 0.9% of zinc with the remainder being magnesium, as well as of 4.5 to 5.3% of aluminum, 0.28 to 0.5% of manganese with the balance being magnesium. The aluminum content of the alloy determines its tensile strength and hardness while the manganese content influences its corrosion resistance.

Magnesium is an element the human body essentially needs and which is completely unobjectionable physiologically. On the other hand, the use of aluminum in implants is controversially discussed due to the fact that aluminum ions may be injurious to health and lead to dementia and loss of memory. Furthermore, aluminum is considered a risk factor for Alzheimer's disease. In this respect, the use of aluminum in bioresorbable stents from which aluminum ions are necessarily liberated is to be viewed as an undesirable risk.

Although rare earth metals in ionic form may act as an anticoagulant when present in higher concentrations, they are to be viewed as unobjectionable, however, when only small amounts of them exist. Iron, zinc and manganese ions are essential trace elements and thus to be considered unobjectionable physiologically.

When manufacturing resorbable magnesium-containing stents the chemical as well as mechanical properties of magnesium and its alloys have also to be taken into account. From a chemical viewpoint, magnesium is an easily corrodible material which is completely dissolved in the human vascular system within a short time span without any protective measures being necessary. The dissolution time can be influenced via the alloying metals.

A chemical problem associated with the use of magnesium in stents is that hydrogen gas is produced during the resorption process which is basically in conflict with the practical application of such magnesium stents for cardiological purposes. Hydrogen gas in the form of small bubbles may cause embolism and thus be hazardous and injurious to the health of patients.

A rapid resorption may be counteracted by adding other alloying metals which enables controlled dissolution characteristics to be achieved. Good results are obtained by adding manganese in an amount of up to 0.5% w/w. Nevertheless, the service life of such alloys for implants having a supporting function, for example in order to stabilize fractures or expanding coronary blood vessels, is much too short in many cases.

To make sure the implants can perform their supporting function fully, in particular in the context of manufacturing medical nails, it is mandatory that they have fatigue strength during the initial phase which should last from several weeks to some months. While magnesium alone does not provide adequate strength, magnesium-aluminum alloys enable the required strength characteristics to be achieved and if manganese is added fatigue strength as well will be adequate in most cases. Another requirement is deformability and ductility of the alloy which is of significance particularly for the placement process of the manufactured stents. After production the stents are crimped out of a tube onto a dilatation balloon and during placement in the vessel mechanically expanded to an extent exceeding the former tube diameter. To cope with the mechanical strains thus acting on the stent the material must have good cold-forming properties so that after placement the magnesium-containing stent is well anchored in the blood vessel without having suffered structural damage worthy of note. Structural damage will constitute starting points for corrosion and in the end cause the construct to dissolve or weaken prematurely. As a rule, magnesium alloys having an aluminum content of less than 10% w/w have both adequate strength as well as deformability.

For that reason and taking into account what has been said hereinbefore there is need to provide a material for the production of implants that does not have the disadvantages of prior-art implants made of resorbable metal alloys as described earlier.

It is thus the objective of the present invention to provide an implant made of a magnesium alloy which can be resorbed by the human or animal body, is free from aluminum, only causes insignificant, if any, amounts of hydrogen to form during resorption and possesses the required stability.

Surprisingly, it has now been found that this objective is achieved by providing an implant of the kind first mentioned above, said implant being made of metallic material comprising a magnesium alloy consisting of at least 96% w/w of magnesium, at least 1% w/w, of manganese and at least 0.5% w/w of at least one metal of the rare earth group.

Rare earth metals in this context are scandium, yttrium and lanthanum as well as the elements of the periodic table of elements following lanthanum, i.e. so-called lanthanides. These elements are in particular cerium, praseodymium, neodymium, promethium, samarium, europium, gadolinium, terbium, dysproslum, holmium, erbium, thulium, ytterbium and lutetium, with preference being given to cerium.

According to the invention the metallic material of the implants may consist of solid structures, lattice structures, wire or fabric structures as well as of metal foam or porous metal. The resorbable metallic material may be combined with is other non-organic materials, for example with ceramic materials or bioglass.

The implants proposed by the present invention are, for example, vascular or non-vascular stents.

Spongy or porous structures offer advantages in that they permit a higher resorption speed, with the existing pores being conducive to the ingrowth of the body's own tissue. This allows the use of magnesium sponge bodies as placeholders, for example for the treatment of fractures and to augment bone or other tissue of the body.

It goes without saying that structure and strength of the metallic material used for the inventive implants are adapted to suit their placement site and purpose, for instance as far as their mechanical properties and/or use as drug delivery systems are concerned.

Especially when used as a replacement for bones the resorbable metallic materials may be suitably processed and so precisely adapted to the requirements of the placement site, for example by laser sintering based on CAD data, and then accurately fitted in the desired location. In this manner cheekbones, areas of the skullcap and similar parts can be remodeled which need to be replaced as a result of accidents or surgical treatments.

The implants proposed by the present invention may consist altogether or partly of such a resorbable metallic material. Aside from the inventive resorbable metallic material such materials may be other resorbable or non-resorbable metallic or non-metallic materials. Such further components may in particular also be plastic materials consisting of a resorbable substance, for example a polylactide or polyglycolide. Resorbable plastic materials of this nature are often used for the purpose of coating stents and are put on the market under the tradename of Resomer® by the company of Boehringer Ingelheim. Moreover, chitin and chitosan biopolymers can be used for coating purposes as well. Coatings frequently serve as substrate for medical substances which by this method are gradually released and dispensed into the surrounding area.

The resorbable metallic materials may also be blended into a curable paste in the form of a powder, for example thus forming part of a mixture with a Resomer®, chitin or chitosan biopolymer, hyaluronic acid, alginate or chondoitrin sulfate, and as such used for augmentation but also sutural sealing purposes in the intestinal area. At the placement site the cured and hardened implant serves a supporting as well as protective function but at the same time permits a defect or suture to heal up before said implant is resorbed by the body.

Preferably, the resorbable magnesium alloy according to the invention consists of 96 to 97.9% w/w of magnesium, 1.6 to 2% w/w of manganese and 0.5 to 2% w/w of rare earth metal. For this purpose, neodymium or cerium is preferably used as rare earth metal. In particular, a composition comprising 97.45% w/w of magnesium, 1.8% w/w of manganese and 0.75% w/w of cerium has proved its worth. Especially for vehicle manufacturing applications such an alloy has been successfully used for holders, supports, seat-, window- or door frames, casings, carriers and miscellaneous parts, and was described in publication DE 202 02 591 U1. Medical uses of this alloy have hitherto not been reported.

The inventive magnesium alloys are characterized by good strength as well as cold workability properties. In contrast with the magnesium alloys herein described earlier these alloys are significantly more resistant to corrosion so that they also can fulfill their supporting function for a longer period of time, that is for approximately three to nine months. In this connection the corrosion resistance can be influenced by appropriately adjusting the manganese content as desired, i.e. the lower the manganese content the higher the resorption speed.

Surprisingly, it has moreover been found that also the inherent tendency of the known magnesium alloys used for implantation purposes towards developing hydrogen during the resorption process is substantially reduced. For one thing, this is due to the significantly increased resistance—although the formation of hydrogen occurs it continues over a much longer period of time—but also to the addition of manganese to the alloy which appears to be conducive to other corrosion paths.

Unexpectedly, it was found as well that a minor content of manganese particularly in an amount of between 1.6 and 2% w/w causes the strength characteristics of magnesium to substantially improve so that the addition of aluminum can be dispensed with.

The magnesium alloys used as proposed by the present invention allow, in particular, the production of medical nails, screws or plates intended for the fixation of fractures. As a result of this, it will no longer be necessary to remove the implanted aids when the fracture has healed; the relevant metallic components will have entirely disappeared from the boy after a long enough time span, said period may range between several months and a few years depending on volume and surface of the components.

The inventive implants can furthermore be put to use in the form of sheets, fabrics and/or nets to be used for the temporary stabilization of tissue, for example when wounds need to be sealed, in the digestive tract or for the treatment of hernia. The sheets may be present in perforated form while the nets may be cut from sheets. It is to be understood, however, that said fabrics and nets may also be composed of filaments which are formed out of the resorbable metallic material. Moreover, the resorbable metallic materials can be processed to form filaments for use as suture material.

Preferred field of application is the making of vascular implants, for example stents. In a manner known per se the stents are cut from tubes manufactured from the relevant magnesium alloy, for example by means of an extrusion process. Having cut the stent to size it can be crimped onto a dilatation balloon by means of a method known per se and together with said balloon transferred to the placement site.

It is to be understood that these magnesium alloys may also be employed for to vascular implants of other form and design, for instance as part of closure systems adopted for heart wall defects.

In a manner known per se the stents can be coated with a plastic material with a view to influencing their dissolving behavior or dispensing a medical substance out of the plastic layer, for example from a bioresorbable Resomer® or chitosan/chitin as described hereinbefore. Such drug eluting stents (DES) have been known for a long time and in many cases provided with proliferation-inhibiting medical agents. Such proliferation-inhibiting medical substances have often been described, mostly employed are rapamycin and paclitaxel. However, this does not mean the use of other kinds of therapeutically expedient active agents is precluded.

The invention furthermore relates to the use of the magnesium alloys described hereinbefore for medical implants, in particular as medical nails, screws or plates for the fixation of fractures and as well for vascular and non-vascular implants and especially stents. The stents may be coated in a manner and by methods known per se, and such a coating may in particular consist of a resorbable Resomer®, and said coating may contain a proliferation-inhibiting drug, especially rapamycin or paclitaxel.

The invention claimed is:

1. Implant consisting of a material resorbable by the body, wherein the metallic material being a magnesium alloy consisting of 96 to 97.9% w/w of magnesium, 1.6 to 2% w/w of manganese and 0.5 to 2% w/w of rare earth metal.

2. Implant according to claim 1, characterized in that the rare earth metal is neodymium or cerium.

3. Implant according to claim 2, characterized in that the implant consists of 97.45% w/w of magnesium, 1.8% w/w of manganese and 0.75% w/w of cerium or neodymium.

4. Implant according to claim 1 in the form of a stent, screw or plate for the fixation of fractures.

5. Implant according to claim 1 in the form of a vascular implant.

6. Implant according to claim 5 in the form of a stent.

7. Implant according to claim 6 in the form of a stem coated with a resorbable biopolymer.

8. Stem according to claim 7, characterized in that said coating contains a proliferation-inhibiting active agent.

9. Stent according to claim 8, characterized in that the resorbable plastic material contains rapamycin or paclitaxel.

* * * * *